United States Patent
Cho

(10) Patent No.: US 9,803,169 B2
(45) Date of Patent: Oct. 31, 2017

(54) MICROPLATE-BASED APPARATUS FOR MEASURING CELL METABOLISM

(71) Applicants: DK Innotech Co., Yangsan-si (KR); Kyung Jin Cho, Busan (KR)

(72) Inventor: Kyung Jin Cho, Busan (KR)

(73) Assignees: DK Innotech Co., Yangsan-si (KR); Kyung Jin Cho, Busan (KR)

(*) Notice: Subject to any disclaimer, the term of this patent is extended or adjusted under 35 U.S.C. 154(b) by 118 days.

(21) Appl. No.: 14/934,809

(22) Filed: Nov. 6, 2015

(65) Prior Publication Data

US 2016/0369222 A1 Dec. 22, 2016

(30) Foreign Application Priority Data

Jun. 17, 2015 (KR) .................. 10-2015-0086193

(51) Int. Cl.
| | |
|---|---|
| *C12M 1/34* | (2006.01) |
| *C12M 1/32* | (2006.01) |
| *C12M 1/36* | (2006.01) |
| *C12M 3/00* | (2006.01) |

(52) U.S. Cl.
CPC ............ *C12M 41/34* (2013.01); *C12M 23/12* (2013.01); *C12M 23/42* (2013.01); *C12M 41/26* (2013.01); *C12M 41/48* (2013.01)

(58) Field of Classification Search
CPC ...... C12M 41/34; C12M 23/12; C12M 41/26; C12M 29/00; C12M 41/48; C12M 23/38
See application file for complete search history.

(56) References Cited

U.S. PATENT DOCUMENTS

| | | | | |
|---|---|---|---|---|
| 5,858,769 A | * | 1/1999 | DiGuiseppi et al. | .. C12M 23/08 435/286.2 |
| 6,673,532 B2 | * | 1/2004 | Rao | ........................ C12M 23/12 435/287.1 |
| 8,809,040 B2 | * | 8/2014 | King et al. | ......... G01N 21/6428 435/287.1 |
| 9,012,209 B2 | * | 4/2015 | Eden et al. | ........... B01L 3/5082 422/73 |
| 2009/0093046 A1 | * | 4/2009 | Kiyota | ................... C12M 41/14 435/288.7 |
| 2010/0297744 A1 | * | 11/2010 | Rhee et al. | ........... B01L 3/5085 435/287.2 |
| 2012/0064564 A1 | | 3/2012 | Grassl et al. | |

FOREIGN PATENT DOCUMENTS

| | | |
|---|---|---|
| JP | 2006-090836 A | 4/2006 |
| JP | 2013-541000 A | 11/2013 |
| KR | 10-2008-0064422 A | 7/2008 |
| KR | 10-2009-0114546 A | 11/2009 |
| KR | 10-1155136 B1 | 6/2012 |

* cited by examiner

*Primary Examiner* — Gautam Prakash
(74) *Attorney, Agent, or Firm* — NSIP Law

(57) ABSTRACT

A microplate-based apparatus for measuring cell metabolism is provided. The apparatus is capable of providing automation of all procedures, ranging from drug injection into each well of a microplate to the measurement of dissolved-oxygen (DO) concentration and hydrogen ion concentration.

7 Claims, 12 Drawing Sheets

MICROPLATE-BASED APPARATUS FOR MEASURING CELL METABOLISM

CROSS-REFERENCE TO RELATED APPLICATION(S)

This application claims priority from Korean Patent Application No. 10-2015-0086193, filed on Jun. 17, 2015, in the Korean Intellectual Property Office, the disclosure of which is incorporated herein by reference in its entirety.

BACKGROUND

1. Field

The following description relates to an apparatus for measuring cell metabolism, and more particularly, to an apparatus for measuring cell metabolism by detecting dissolved-oxygen (DO) concentration and hydrogen ion concentration (pH).

2. Description of the Related Art

Korean Patent Registration No. 10-1155136 discloses a multi-channel photobiological reactor for culture of photosynthetic microorganisms. This reactor uses a multi-channel microplate with a plurality of wells for the search and optimization of photosynthetic strains and faster bioprocess development. Furthermore, the reactor sets up an optimal environment for the bioreaction through agitation and precise temperature control.

DO concentration and a pH, which are important variables in various fields, are required for monitoring (e.g., a quality of drinking water, freshness of food, and cell activation in a bioreactor) and maintaining the optimal conditions for reactions. In addition, the analysis of DO concentration and a pH is essential in clinical analysis and research of physiological material, such as blood, and sea water analysis and research.

SUMMARY

The following description relates to an apparatus for measuring cell metabolism which is capable of providing automation of all procedures, ranging from drug injection into each well of a microplate to the measurement of dissolved-oxygen (DO) concentration and hydrogen ion concentration.

In one general aspect, there is provided an apparatus for measuring cell metabolism, including: an X-Y DRIVING stage table movable horizontally and vertically; a microplate which comprises a plurality of wells and is mounted on the top of the X-Y DRIVING stage table, each of the wells accommodating cells and comprising a dissolved oxygen (DO) sensing film and a hydrogen ion concentration (pH) sensing film; a sensor board which is situated on the top of the X-Y DRIVING stage table and comprises pairs of a light emitting element and a light detecting element for DO detection, each pair vertically corresponding to the DO sensing film in each well of the microplate mounted on the X-Y DRIVING stage table, and pairs of a light emitting element and a light detecting element for pH detection, each pair vertically corresponding to the pH sensing film in each well; a plurality of cartridges containing drugs; a plurality of infusion pumps disposed at fixed positions and configured to inject the drugs supplied from the cartridges through nozzles to the wells of the microplate; and a controller configured to control movement of the X-Y DRIVING stage table and measure DO concentration and a pH with respect to at least one well of the microplate.

The DO sensing film and the pH sensing film may be fluorescent sensor films.

The plurality of cartridges may be provided on an upper portion of a housing of the apparatus.

The apparatus may further include a sealing cover configured to hermitically seal all wells of the microplate.

The sealing cover may be vertically movable by controlling a motor drive thereof.

The apparatus may further include a light shielding plate positioned between the microplate and the sensor board and including holes that correspond to the light emitting elements and the light detection elements for both DO detection and pH detection, respectively.

The light shielding plate may include a plurality of filters that allow light emitted from the DO sensing film and light emitted from the pH sensing film to pass through the holes of the light shielding plate.

The apparatus may further include a memory configured to store user-defined protocols for each well. The controller may control: movement of the X-Y DRIVING stage table; drug injection into each well; and measurement of DO concentration and pH in each well at a designated measurement time.

Other features and aspects will be apparent from the following detailed description, the drawings, and the claims.

BRIEF DESCRIPTION OF THE DRAWINGS

FIG. 8 is a diagram illustrating an on-screen allowing for input of a user-defined protocol.

Figure 1:
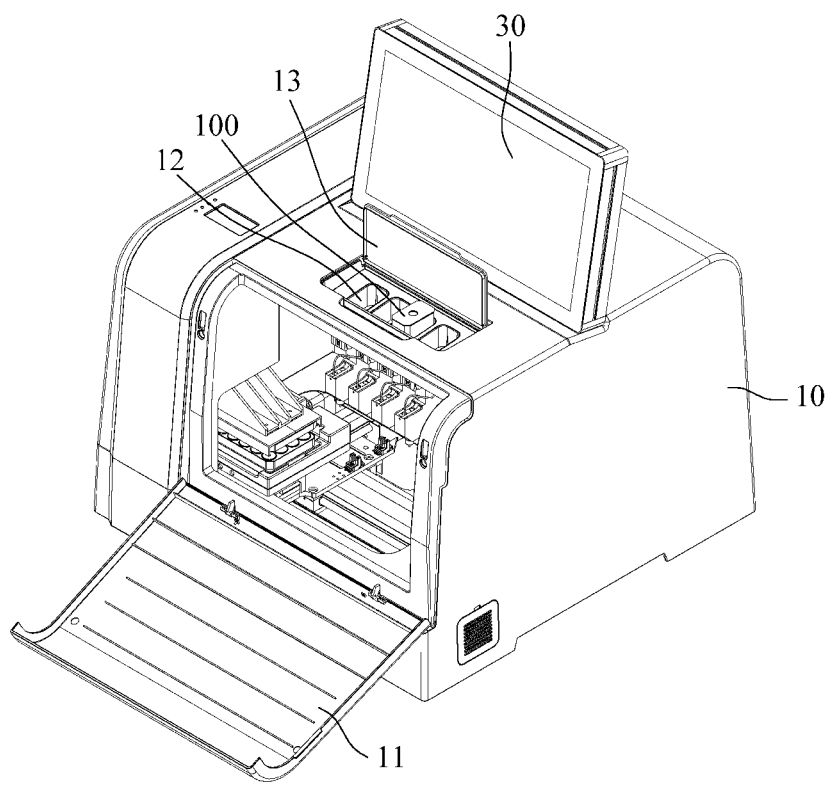
FIG. 1 is a perspective view of an apparatus for measuring cell metabolism according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Figure 2:
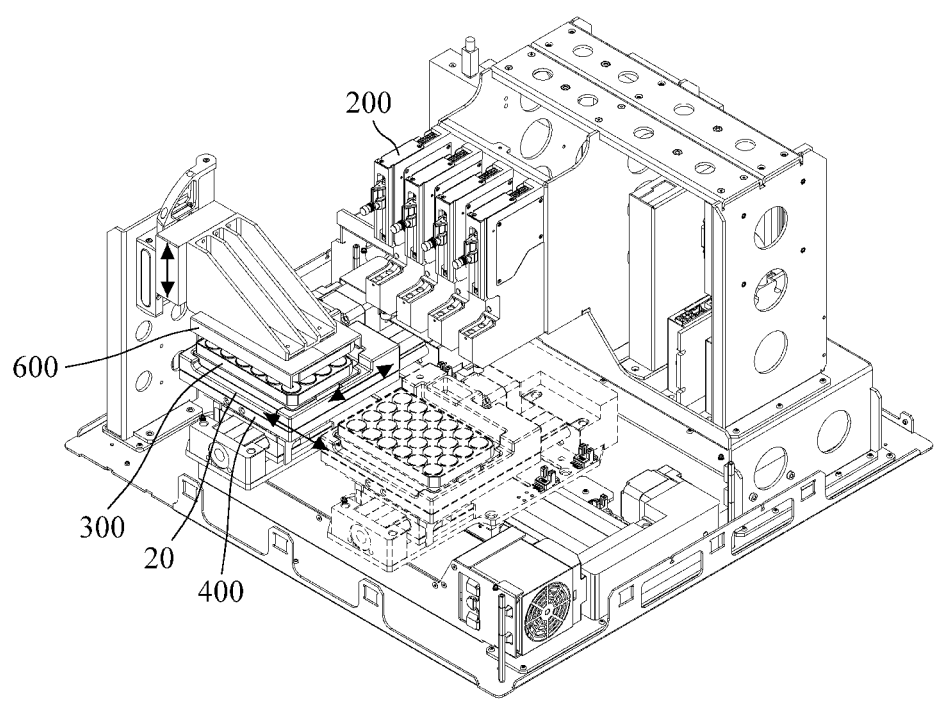
FIG. 2 is a perspective view of the internal configuration of a housing of the apparatus of FIG. 1.
Figure 3:
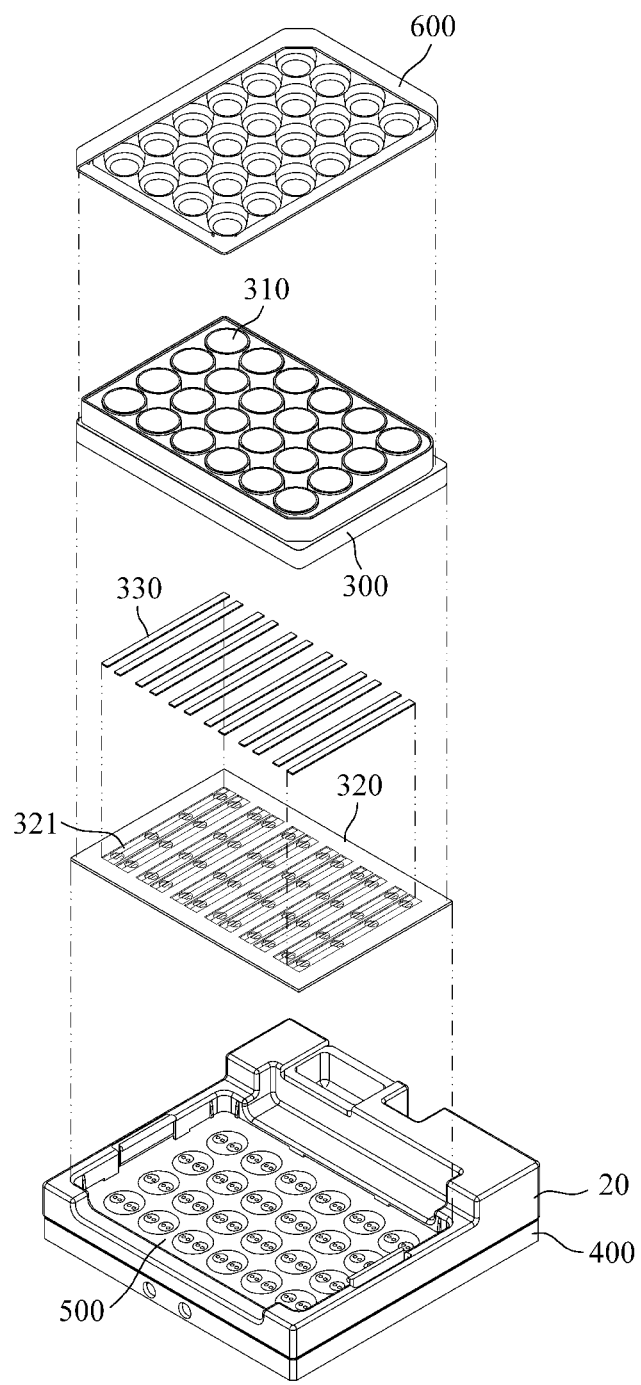
FIG. 3 is a partial exploded view of the internal configuration of the housing of FIG. 2.
Figure 4:
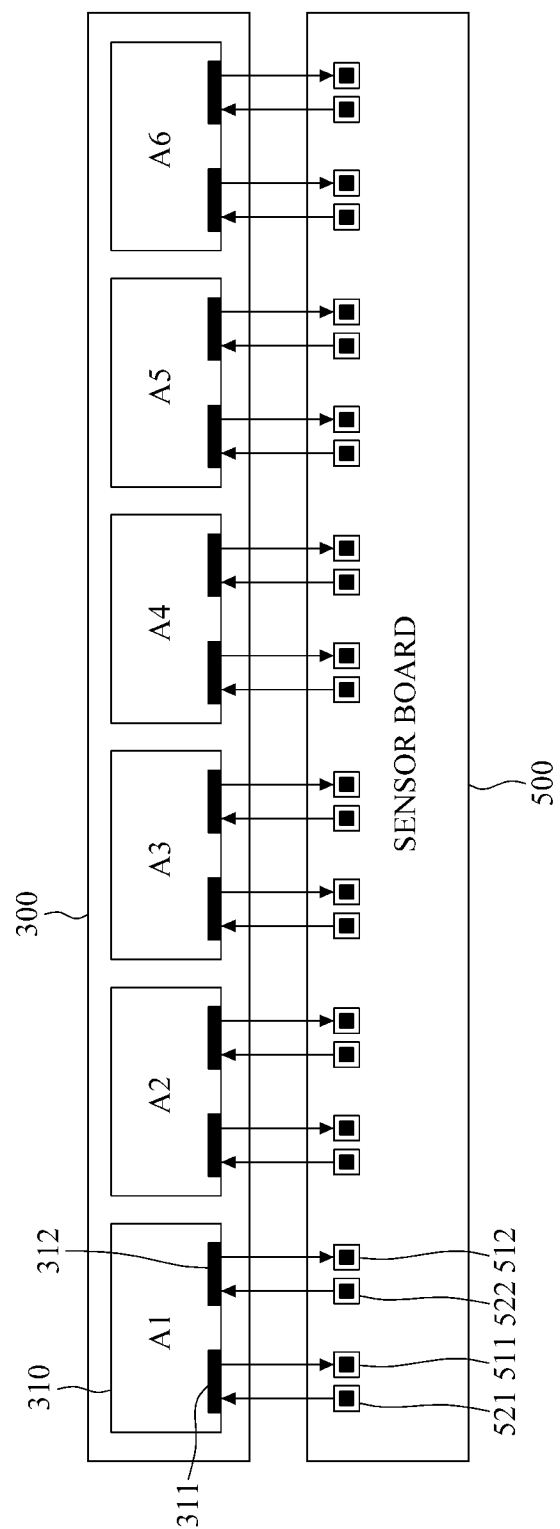
FIG. 4 is a block diagram illustrating a microplate and a sensor board of the apparatus according to the exemplary embodiment.

FIG. 1 is a perspective view of an apparatus for measuring cell metabolism according to an exemplary embodiment; FIG. 2 is a perspective view of the internal configuration of a housing of the apparatus of FIG. 1; FIG. 3 is a partial exploded view of the internal configuration of the housing of FIG. 2; and FIG. 4 is a block diagram illustrating a microplate and a sensor board of the apparatus according to the exemplary embodiment.

Said cell metabolism-measuring apparatus measuring cell metabolism includes a housing that surrounds equipment and electronic parts. The housing 10 houses equipment and electronic parts, such as a cartridge 100, infusion pumps 200, a microplate 300, an X-Y DRIVING stage table 400, and the sensor board 500. As shown in FIG. 1, the housing 10 may include a front cover 11 that opens and closes, have a plurality of cartridges 100, or have only one cartridge; the housing 10 may be physically partitioned to have multiple accommodation spaces. In one exemplary embodiment, the housing 10 has one or more mounting holes 12 to mount the cartridge 100 onto an upper portion thereof, and it is on to this mounting hole 12 that the cartridge 100, which contains a drug, is situated. As shown in FIG. 1, there may be four mounting holes 12, in each of which the cartridge 100 can be situated. The housing 10 may include a hole cover 13 to cover the mounting holes.

The four cartridges 100, may each contain drugs, selected by a user for an experiment, which may be different from each other; the drug may be, for example, Oligomycin 2, 4-Dintrophenol (2, 4-DNP), Carbonyl cyanide p-trifluoromethoxyphenylhydrazone (FCCP), Rotenone, or Antimycin A. The cartridges 100 are connected to the respective infusion pumps 200 via pipes, and the drug is supplied to each of the securely positioned infusion pump 200 through the pipes.

The purpose of infusion pumps 200 is to inject drugs into wells of the microplate 300. In one exemplary embodiment, each infusion pump 200 is a syringe pump having a 3-way valve. A plurality of infusion pumps 200 are provided, and the number of infusion pumps 200 may be equal to the number of cartridges 100 or the physically partitioned accommodation spaces. Each of the infusion pumps 200 is connected to each cartridge 100 via each pipe. The infusion pumps 200 carries drugs, supplied from the cartridges 100 through the pipes, and dispenses the said drugs.

The microplate 300, also referred to as a microtiter plate, has multiple wells 310, and the number of wells may be, for example, 6, 12, 24, 48, 96, or the like. In the illustrated example, the microplate 300 is a 24-well microplate. The 24 wells may be formed in 4 rows and 6 columns (A1~A6, B1~B6, C1~C6, D1~D6). Each well 310 accommodates cells, and includes a dissolved oxygen (DO) sensing film 311 and a pH sensing film 312. The DO sensing film and the pH sensing film each may be a fluorescent sensor film which is coated with florescent dye. Tris (4,7-diphenyl-1,10-phenanthroline) ruthenium (II), Ru (dpp)32+ (hereinafter, referred to as "Rudpp") may be used as the florescent dye for the DO sensing film, and hydroxypyrene-1,3,6-trisulfonic acid trisodium salt (HPTS) may be used as the florescent dye for the pH sensing film 312.

Among various fluorescent dyes used in oxygen detection, Rudpp exhibits a strong fluorescence emission and has superior fluorescence quantum yield and fluorescence duration. DO detection by use of Rudpp is based on fluorescence decay caused by oxygen molecule. The fluorescence decay takes place when the energy emitted during the excited fluorescent dye dropping to the ground state is absorbed by the oxygen molecule, resulting in consumption of the emitted energy and reduction in intensity of fluorescence. The reduced intensity of fluorescence is inversely proportional to the concentration of oxygen molecules. That is, the Rudpp is excited by light of 480 nm and emits 600-nm fluorescence as it falls to the ground state. HPTS used for pH detection can produce a strong fluorescence and is non-toxic. The pH detection using fluorescence uses a principle that fluorescence is emitted when a fluorescent dye is protonated or deprotonated by acid or alkali. When light of 405 nm is emitted to the HPTS, the HPTS absorbs electrons and is excited; as it returns to the ground state, the HPTS emits 510-nm fluorescence.

The X-Y DRIVING stage table 400 is a table integrated with an X-Y DRIVING stage. The X-Y DRIVING stage table 400 can move the microplate in X-axis and Y-axis directions, i.e., in horizontal directions, such as, forward, backward, left and right, in response to the driving of the X-Y DRIVING stage. The X-Y DRIVING stage table 400 has the microplate 300 placed on its top portion. The microplate 300 accordingly can move along the X-axis and the Y-axis, and thus a specific well 310 of the microplate 300 can be placed below one of the infusion pumps 200 by controlling the movement of the X-Y DRIVING stage table 400. This means that an intended drug can be automatically injected in each well 310. In addition, the drug in the well 310 can be agitated according to the movement of the X-Y DRIVING stage table 400. In other words, the controller may control the movement of the X-Y DRIVING stage table for the purpose of agitation.

The sensor board 500 which is mounted to the sensor housing 20 is integrally provided to the top portion of the X-Y DRIVING stage table 400. The microplate 300 is placed on the sensor board 500. The sensor board 500 includes pairs of a light emitting element 521 and a light detecting element 511 for DO detection, each of pairs vertically corresponding to the DO sensing film in each well 310. The sensor board 500 also includes pairs of a light emitting element 522 and a light detecting element 512 for pH detection, each of pairs vertically corresponding to the pH sensing film in each well 310. The light emitting elements may be light emitting diodes and the light detecting elements may be photodiodes or phototransistors. When the light emitting element 521 for DO detection emits light toward the microplate 300, the fluorescent DO sensing film emits fluorescence, and the light detecting element 511 for DO detection receives the emitted fluorescence. When the light emitting element 522 for pH detection emits light, the fluorescent pH sensing film emits fluorescence and the light detecting element 512 for pH detection receives the emitted fluorescence.

Although not illustrated in FIGS. 1 to 4, a controller 700 controls the overall operation of the apparatus, and may be formed by including at least some of the following elements: one or more processors, field-programmable gate array (FPGA), a micro control unit (MCU) and the like. The controller 700 may be provided as a single controller, or provided as multiple controllers. In the latter case, the controller 700 may consist of a primary controller, as well as an auxiliary controller that is placed in remote and capable of data transmission/reception to the primary controller. The controller 700 may control the movement of the X-Y DRIVING stage table 400 and driving of the infusion pumps 200, as well as control optical measurement. In addition, a signal with respect to at least one well 310 of the microplate 300 is received by the light detecting element of the sensor board 500 and then is converted into an electrical signal. DO concentration and pH are measured by analyzing the electrical signal. Besides of the above described operations, the controller 700 may perform other controlling functions for operating the apparatus.

According to an additional aspect, the apparatus may further include a light shielding plate 320. The light shielding plate 320 is positioned on the sensor board 500, or more specifically, between the sensor board 500 and the microplate 300. In one exemplary embodiment, the light shielding plate 320 may be a black plastic plate to shield the light. The light shielding plate 320 includes holes that correspond to the respective light emitting elements 521, 522 and light detecting elements 511, 512 for both DO and pH detection. Accordingly, the light emitted from the light emitting elements and the fluorescent sensor films are transmitted through the holes.

Furthermore, the light shielding plate 320 may further include multiple filters 330. The filters 330 are bandpass filters that pass the fluorescence from the DO sensing film or pH sensing film. In the case of 24-well microplate aligned in 4 rows and 6 columns, 6 filters 330 may be provided as shown in FIG. 4. The filters 330 allow the fluorescence from the fluorescent sensor films to pass through the holes of the light shielding plate 320. The light shielding plate 320 may have filter grooves 321 formed on areas in which the holes corresponding to the light detecting elements 511 for DO detection and the holes corresponding to the light detecting elements 512 for pH detection are placed, as shown in FIG. 4, and the filters 330 are respectively fit into the filter grooves 321.

According to another aspect, the apparatus may further include a sealing cover 600. The sealing cover 600 is a cover to hermetically seal all wells 310 of the microplate 300. As shown in FIG. 3, a lower portion of the sealing cover 600 is formed to have projections corresponding to the respective wells 310 so as to completely seal the wells 310, and at least the projections for sealing the wells 310 may be made of rubber. As shown in FIG. 2, the sealing cover 600 may be positioned at one side within the housing 10, and this position is referred to as a measurement position at which DO concentration and pH are measured. In one aspect, the sealing cover 600 is movable along Z-axis, i.e., in a vertical direction. To this end, a Z-axis driving motor is provided. By controlling the driving of the Z-axis driving motor, the controller 700 controls the upward and downward movements of the sealing cover 600. To perform optical measurement with respect to at least one well 310 of the microplate 300, the controller 700 moves the X-Y DRIVING stage table 400 to the measurement position, then moves the sealing cover 600 downward to seal the microplate 300, and thereafter performs optical measurement. Once optical measurement is finished, the controller 700 moves the sealing cover 600 upward so that the sealing cover 600 is separated from the microplate 300. The reason for sealing the microplate 300 is to prevent air from entering the well during optical measurement, thereby ensuring the accurate measurement.

Further, the apparatus may further include a computing device 30. The computing device 30 may be an all-in-one personal computer, and may be provided to the upper portion of the housing 10, as shown in FIG. 2. In the case of the controller consisting of a primary controller and an auxiliary controller, the primary controller may be configured in the computing device 30, and the auxiliary controller may be configured in the sensor board 500. A display module of the computing device 30 may be a touch screen formed by a touch panel that is capable of displaying an image and receiving a user input. Alternatively, the display module may serve only as a display, and an additional means of user input may be provided. The computing device 30 may provide a graphic user interface (GUI), which enables the user to input desired data.

Figure 5:
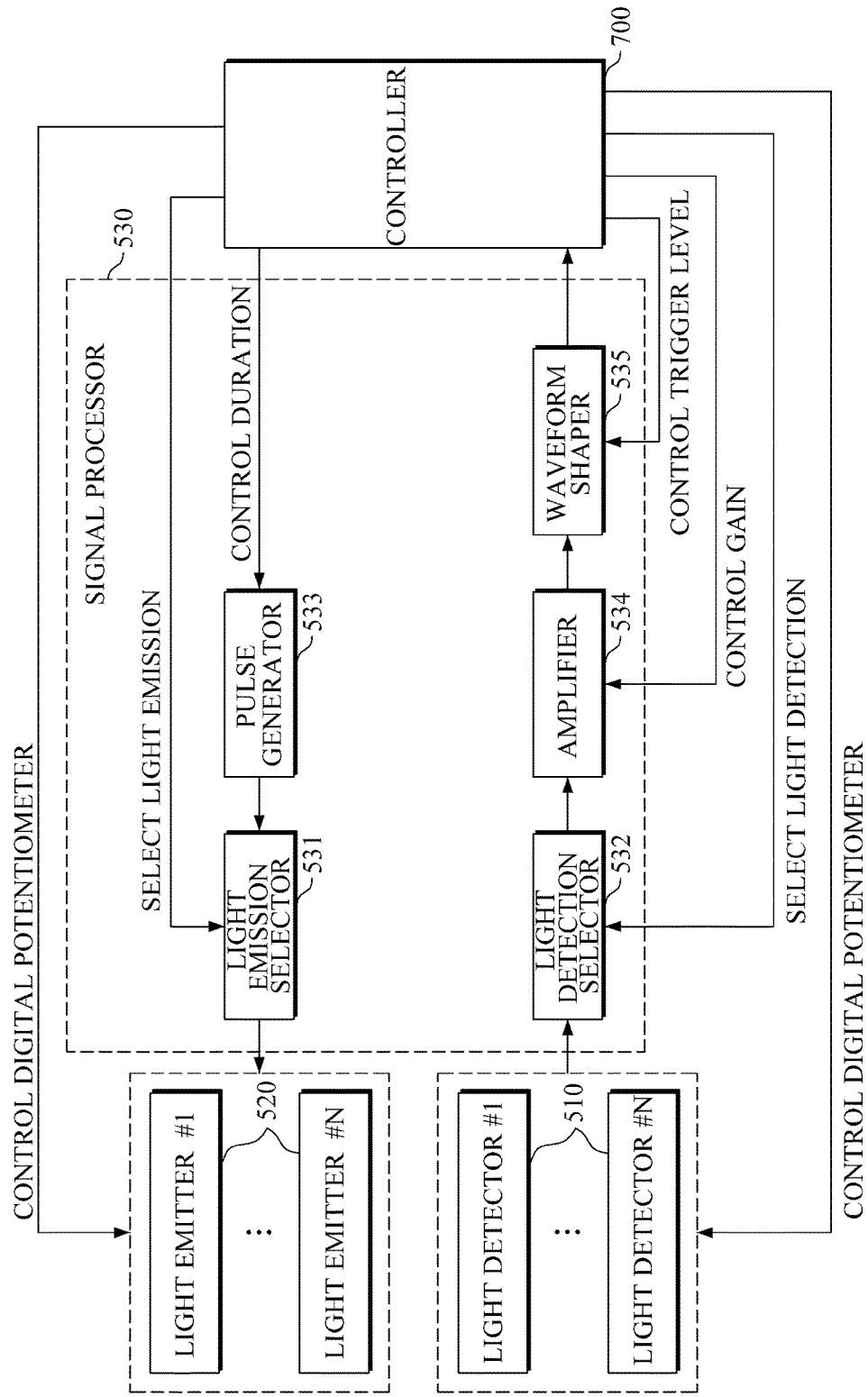
FIG. 5 is a block diagram for explaining optical measurement according to an exemplary embodiment.

FIG. 5 is a block diagram for explaining optical measurement according to an exemplary embodiment. A light emitting array includes a plurality of light emitters 520 formed on the sensor board 500. The number of the light emitters 520 is double the number of wells. Since each well 310 has the DO sensing film 311 and the pH sensing film 312, 2 light emitters 520 are provided for each well 310. Each light emitter 520 may include an LED as a light emitting element, as well as a digital potentiometer capable of adjusting the driving current of the LED. The controller 700 may control the digital potentiometer to adjust the amount of light. The light detecting array further includes a plurality of light detectors 510 formed on the sensor board 500. The number of light detectors 510 is also double the number of wells for the same reason as the light emitters 520. Each light detector 510 may include a photodiode (PD) as a light detecting element, as well as the digital potentiometer capable of adjusting the driving current of the PD.

A signal processor 530 processes both an output signal to be sent to the light emitter 520, as well as an input signal sent from the light detector 510. The signal processor 530 may be configured on the sensor board 500, or be configured on a separate board. As shown in FIG. 5, the signal processor 530 includes a light emission selector 531, a light detection selector 532, a pulse generator 533, an amplifier 534, and a waveform shaper 535. The light emission selector 531 is configured to select one of the light emitters 520, and the light detection selector 532 is configured to select one of the light detectors 510. In one exemplary embodiment, the light emission selector 531 and the light detection selector 532 are both multiplexers. The pulse generator 533 generates and outputs a pulse. The output pulse may be amplified by the amplifier and then be output to the light emitting array. The light emitter 520 which has received the amplified pulse emits light according to the pulse duration. A signal is received by the light detector 510 and input to the amplifier 534 through the light detection selector 532. The amplifier 534 amplifies the received signal and outputs the amplified signal. The waveform shaper 535 shapes the waveform of the amplified signal. In one exemplary embodiment, the waveform shaper 535 is a Schmitt trigger. As is already well-known, the Schmitt trigger compares a voltage of the signal with a reference level (trigger level) and standardizes the voltage to be "1" or "0."

The controller 700 is in charge of all controls regarding optical measurement. In this case, the controller 700 may be an auxiliary controller. The controller 700 may adjust the light intensity of the LED by controlling the digital potentiometer of the light emitter 520, and also adjust the sensitivity of the PD by controlling the digital potentiometer of the light detector 510. The controller 700 may output a light emission selection signal to the light emission selector 531 so that said selector may choose a specific light emitter 520. The controller 700 may also output a light detection signal to the light detector 532 to select a specific light detector 510. In addition, the controller 700 may control the pulse duration of the pulse generator 533, control the amplification gain of the amplifier 534, and as well as control the trigger level for waveform shaping by the waveform shaper 535.

Figure 6:
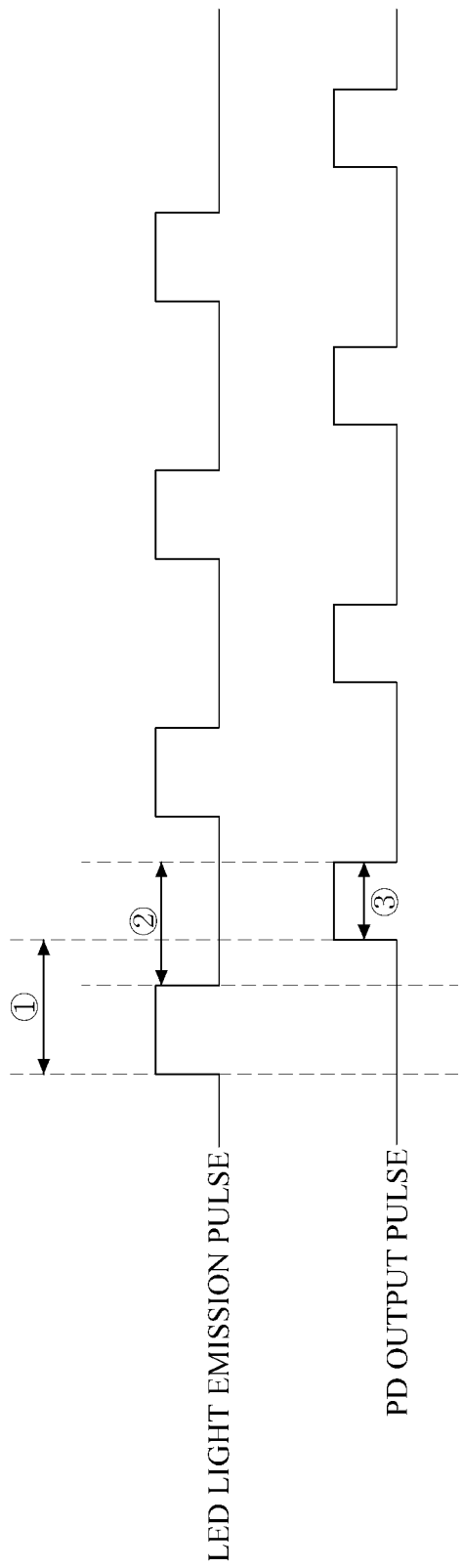
FIG. 6 is a diagram illustrating an example of an LED light emission pulse and a PD output pulse.

The controller 700 measures the fluorescence intensity once the waveform shaper 535 has shaped the waveform of the signal. In one exemplary embodiment, the controller 700 measures the fluorescence intensity using a time delay measurement method. Specifically, the controller 700 measures both the delay of LED light emission pulse and the delay of PD output pulse, as well as obtains the fluorescence intensity from the measured delays. Delay of fluorescence emission is related to the concentration of oxygen molecules and hydrogen ion concentration: it is proportional to the concentration of oxygen molecules and inversely proportional to the hydrogen ion concentration. Hence, the DO concentration and pH can be calculated by measuring the delay time of the fluorescence emission. Referring to FIG. 6, the PD output pulse delay is measured from a LED light emission pulse. For example, a delay time ( ) between the rising edge of the LED light emission pulse to the rising edge of the PD output pulse may be measured; or a delay time ( ) between the falling edge of the LED light emission pulse and the falling edge of the PD output pulse may be measured. In order to enhance the accuracy, the controller 700 may repeat the measurement many times and calculate the average value, thereby obtaining the fluorescence intensity. When calculating the average value, the maximum value and the minimum value can be excluded.

In another exemplary embodiment, the controller 700 measures a duration of the PD output pulse and obtains the fluorescence intensity from the measured duration. If the LED light emission pulse width is fixed, the PD output pulse width varies according to the fluorescence intensity. Since the LED light emission pulse width is already known, the controller 700 may obtain the fluorescence intensity by measuring the PD output pulse width ( ). To improve the accuracy of result, the controller 700 repeats the measurement a number of times and calculates the average value to obtain the fluorescence intensity, wherein minimum and maximum values may be excluded in calculating the average value. In another exemplary embodiment, the controller 700 uses both the time delay measurement method and the PD output pulse width measurement method to obtain the fluorescence intensity. For example, measurement values from the two methods are averaged, and based on the average, the fluorescence intensity may be obtained; or the fluorescence intensity may be obtained by applying different weights to the two methods.

Figure 7:
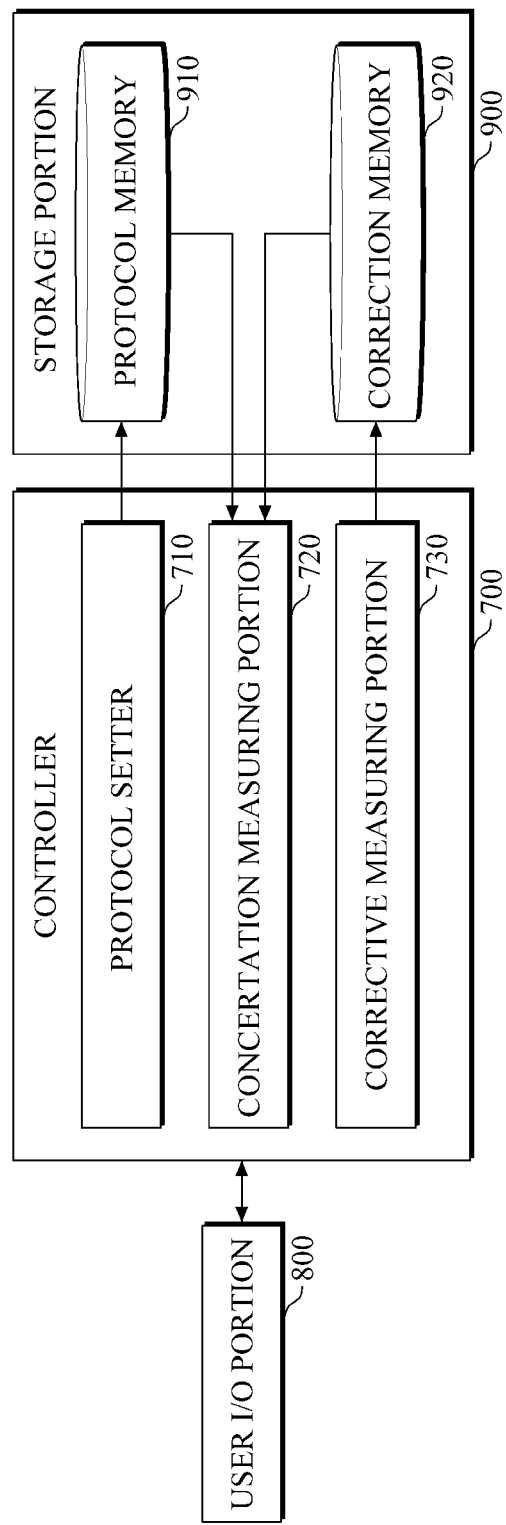
FIG. 7 is a block diagram for explaining the control of an apparatus for measuring cell metabolism according to an exemplary embodiment.

FIG. 7 is a block diagram for explaining the control of an apparatus for measuring cell metabolism according to an exemplary embodiment. A user input/output (I/O) portion 800 includes an input means for user input and an output means for output data. The user I/O portion 800 may not be configured in the apparatus. In this case, the apparatus measuring cell metabolism may be connected to an external computer that serves as a user I/O via communication cables or wireless connections. A storage portion 900 includes one or more memories. The storage portion 900 stores operating programs and control data both for the overall operation of the apparatus. The storage portion 900 includes a protocol memory 910 and a correction memory 920. The protocol memory 910 stores user-defined protocol for each well. The user-defined protocol is information used for automatically performing measurement process of each well. In one exemplary embodiment, the user-defined protocol includes information for each well, such as the amount of injection, a type of drug, and a stand-by time between administration of drug and measurement. The correction memory 920 stores driving information or offset values, which will be described below.

The controller 700, although not illustrated, may be physically divided into a primary controller and an auxiliary controller. The primary controller may be configured in the computing device 30, and the auxiliary controller may be configured in the sensor board 500. The primary controller may be one or more processors, and the auxiliary controller may be a micro control unit (MCU). The auxiliary controller controls operations only related to optical measurement, as described with reference to FIG. 5, and the primary controller controls all the other operations.

As shown in FIG. 7, the controller 700 may include a protocol setter 710 and a concentration measuring portion 720, as well as a corrective measuring portion 730. The protocol setter 710, the concentration measuring portion 720, and the corrective measuring portion 730 may be configured as software modules. The controller 700 may be divided into the primary controller and the auxiliary controller for each software function unit, wherein the configuration for optical measurement may be provided in the auxiliary controller and all the other configurations may be provided in the primary controller. The protocol setter 710, which is configured to set up the user-defined protocol, receives the user-defined protocol, input by the user through the user I/O portion 800 provided on the apparatus for measuring cell metabolism or input from the external computing device, stores the received protocol in the storage portion 900 and completes protocol setup.

Figure 8:
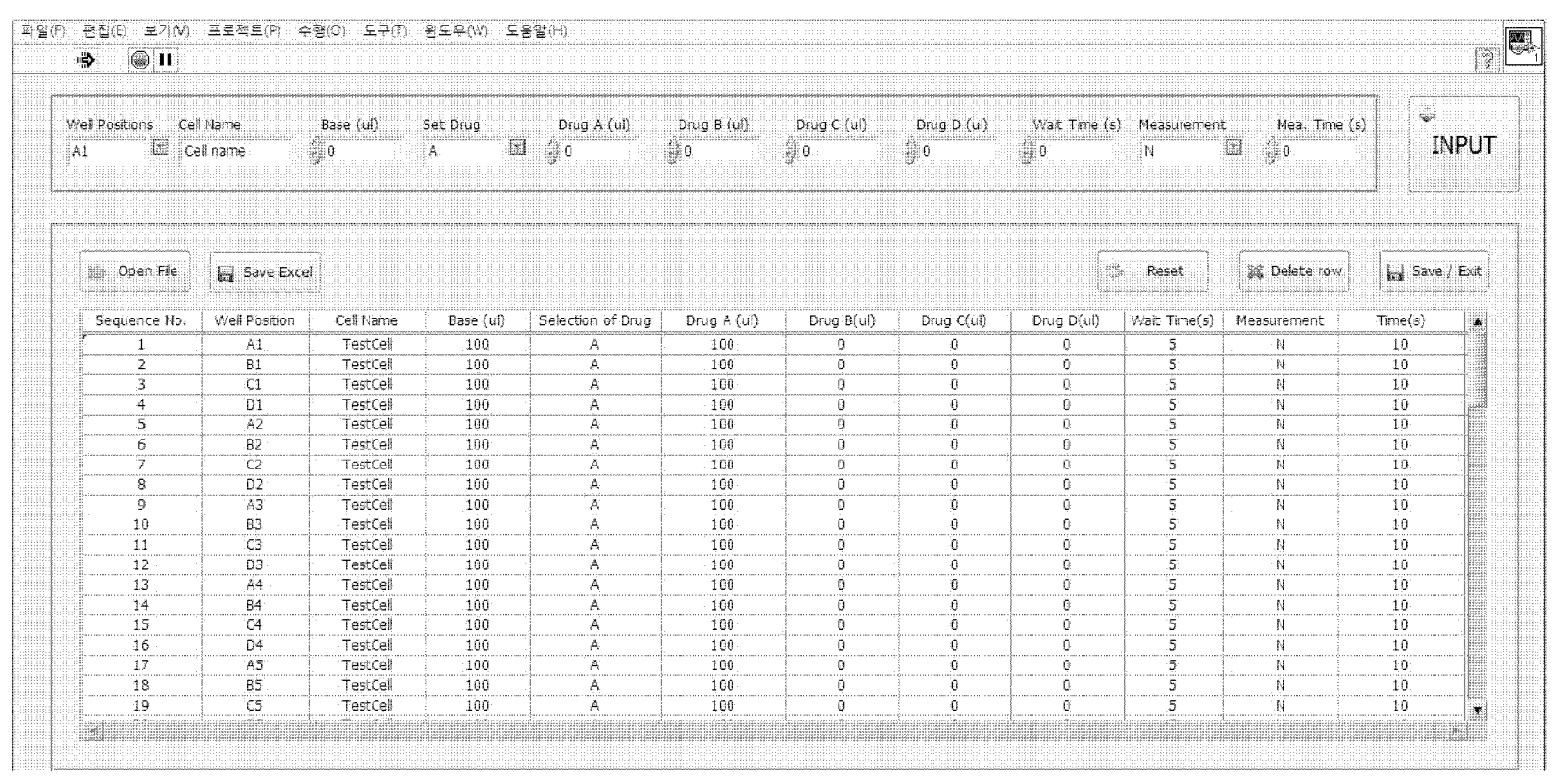

FIG. 8 is a diagram illustrating a spreadsheet screen to allow for input of a user-defined protocol. The user may input, through the spreadsheet, the type of drug, an amount of injection, and a stand-by time between drug administration and measurement as shown in FIG. 8. The protocol setter 710 receives the data a user-defined protocol for each well through the spreadsheet as shown in FIG. 8, and stores the received protocol in the memory 910 to complete the protocol setup.

Figure 9:
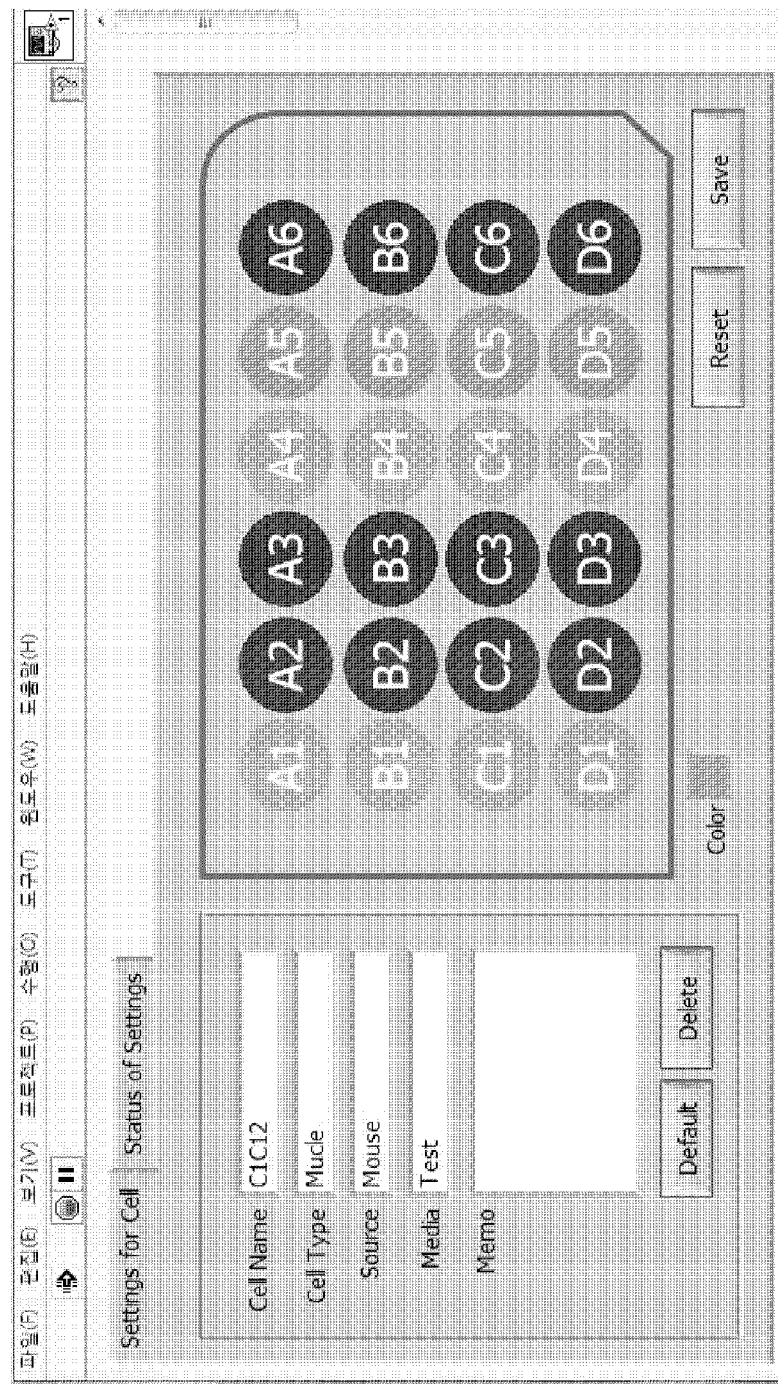
FIG. 9 is a diagram illustrating an example of an on-screen 24-well arrangement.

FIG. 9 is a diagram illustrating an example of a screen for a 24-well arrangement microplate, or more specifically, an image of screen for a 24-well arrangement in 4 row and 6 columns. The user may select a well entity from the screen as shown in FIG. 9 and define a protocol to be applied to the selected well. Or the user may first define a protocol and then select a well entity. The protocol setter 710 may, for example, display an input window to enable the user to input a protocol that includes information for each well about at least one of the following: the amount of injection, the type of drug, drug administration time, and a stand-by time between drug administration and measurement. The input window may be displayed together with the 24-well image shown in FIG. 9. The user may select two or more well entities, and the protocol setter 710 may set up the user-defined protocol to be the same for a group of the selected two or more wells. In addition, groups of wells may be colored with different colors so as to be distinguishable from one another.

The protocol setter 710 may associate the spreadsheet of FIG. 8 with the well arrangement image of FIG. 9. For example, when the user defines protocols using the spreadsheet, the protocol setter 710 applies the defined protocols to the well-arrangement screen image. Conversely, when the user defines protocols using the well arrangement screen image, the protocol setter 710 applies the defined protocol to the spreadsheet.

The concentration measurement portion 720 conducts main measurement process according to the user-defined protocols stored in the protocol memory 910. The corrective measuring portion 730 performs an initial measurement process to improve the accuracy of measurement by the concentration measuring portion 720. It is difficult for all sensors on the sensor board to have the same characteristics due to differences in the manufacturing process, thereby leading to errors in measurement results. Therefore, before conducting the actual measurement, characteristics of all sensors may need to be identified, and then the measurement of DO concentration and pH may need to be conducted. The corrective measuring portion 730 stores, in the correction memory 920, driving information used for driving each sensor whose characteristics have been identified beforehand; or it may store, in the correction memory 920, offset values used for calibration of measurement values.

Figure 10:
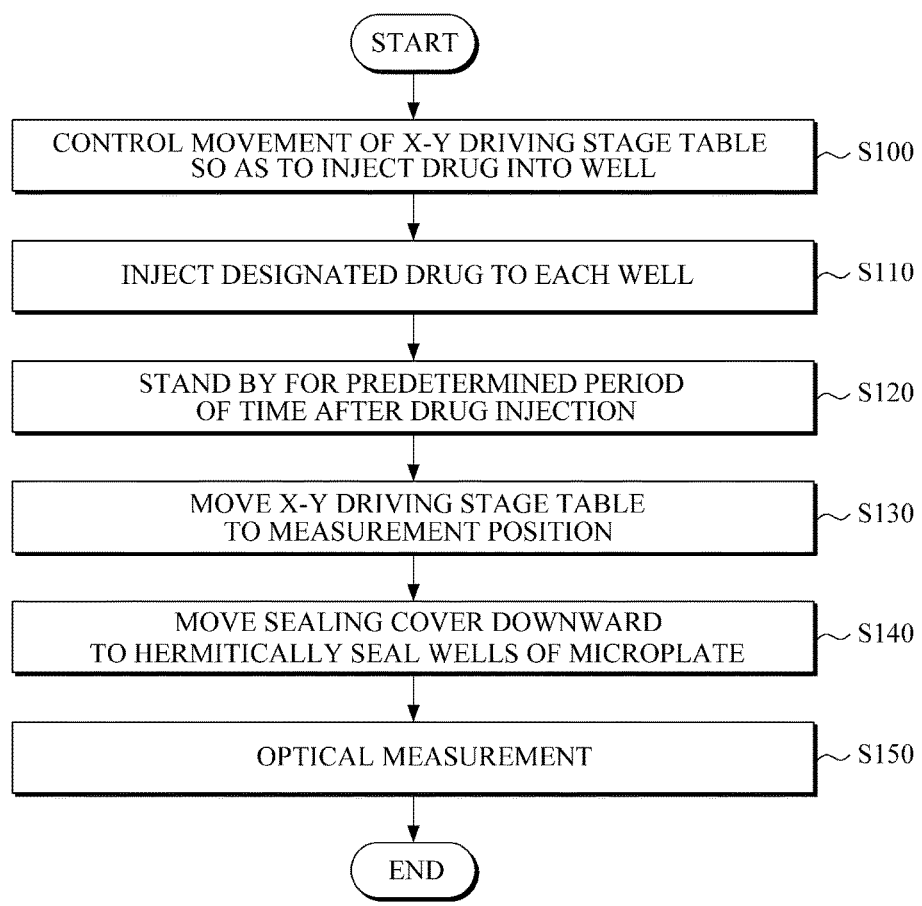
FIG. 10 is a flowchart illustrating a method for measuring DO concentration and pH according to an exemplary embodiment.

FIG. 10 is a flowchart illustrating a method for measuring DO concentration and a pH according to an exemplary embodiment. Referring back to FIG. 7, the concentration measuring portion 720 performs a measurement process according to the user-defined protocol stored in the protocol memory 910. The concentration measuring portion 720 moves the X-Y DRIVING stage table 400 to a specific position in order to inject drugs to each well according to the user-defined protocol for each well, as depicted in S100, and controls the infusion pumps to fill each well with a designated drug, as depicted in S110. If the protocol specifies the drug injection time for each well, the process follows the protocol. Otherwise, the wells are subsequently filled with designated drugs. If the time for injecting a drug is not specified for each well and the wells are assigned sequence numbers as shown in the spreadsheet of FIG. 7, the concentration measuring portion 720 controls the movement of the X-Y DRIVING stage table 400 and the driving of the infusion pumps 200 in order to fill the wells according to the sequence numbers. After injecting the designated drugs into the wells, the concentration measuring portion 720 may stand by for a predetermined period of time for each well so that a biochemical reaction takes place in each well, as depicted in S120. The concentration measuring portion 720 controls the X-Y DRIVING stage table 400 to place in position at a designated measurement time for each well, as depicted in S130. Alternatively, the concentration measuring portion 720 may control the X-Y DRIVING stage table 400 to place in position in advance. In S140, the concentration measuring portion 720 controls the sealing cover 600 so that said cover moves downward at the designated measurement time for each well such that the wells of the microplate 300 seated on the X-Y DRIVING stage table 400 can be hermitically sealed. Then, once the wells of the microplate 300 are sealed completely, the concentration measuring portion 720 measures both DO concentration and a pH by using optical measurement, as depicted in S150.

The concentration measuring portion 720 may control the sealing cover 600 so that said cover moves upward after measurement. In addition, the concentration measuring portion 720 may control the X-Y DRIVING stage table 400 to move to a reference position, or let the X-Y DRIVING stage table 400 to stay at the measurement position. Then, the concentration measuring portion 720 may continue to perform operations until measurement of all wells is finished according to the user-defined protocols. Further, the concentration measuring portion 720 may perform position control for recognizing the reference position of the X-Y DRIVING stage table 400 before conducting the controls according to the user-defined protocol. For example, the concentration measuring portion 720 recognizes the reference position using a limit switch of the X-Y DRIVING stage table. The position recognition technologies are well known, and thus the detailed description thereof will be omitted. In the case of absence of the sealing cover 600, the measurement position may not be specified. In this case, if the wells of the microplate 300 need to be hermitically sealed for measurement, the user may manually cover the microplate 300 with a separate sealing cover. For example, the user may open the front cover and seal the microplate 300 with the front cover.

Figure 11:
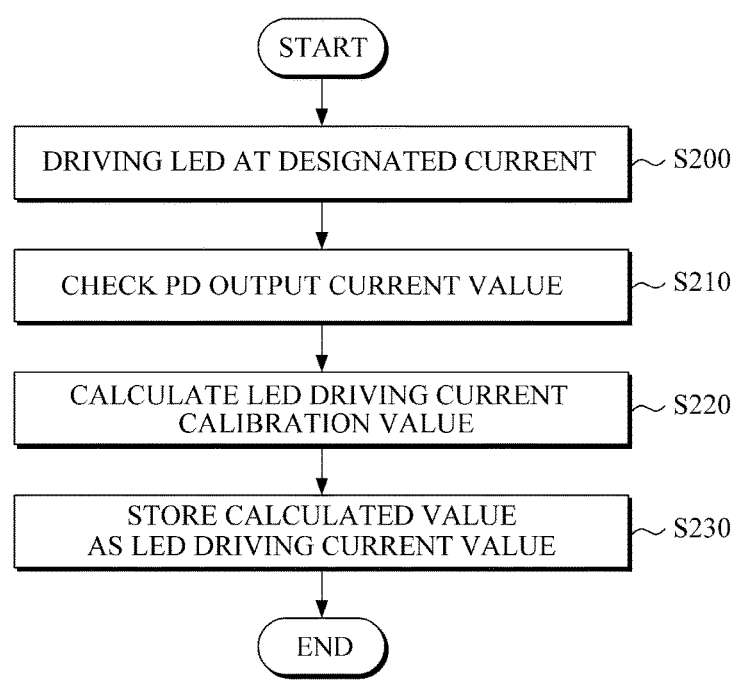
FIG. 11 is a flowchart illustrating a measurement method for identifying sensor characteristics.

FIG. 11 is a flowchart illustrating a measurement method for identifying sensor characteristics. For identifying the characteristics of sensors, the wells of the microplate 300 may be filled with a standard reagent. The standard agent may be contained in the cartridge 100 and injected into the wells of the microplate 300 through the infusion pumps 200. The corrective measuring portion 730 drives the LED at a designated driving current value, as depicted in S200, and checks a resulting PD output current value, as depicted in S210. If the checked PD output current value is different from a reference current value, the corrective measuring portion 730 calculates, based on the difference between the PD output current value and the reference current value, an LED driving current value that is calibrated to allow the PD output current value to be the same as the reference current value, as depicted in S220. Then, the corrective measuring portion 730 stores the calculated LED driving current value as driving information in the correction memory 920, as depicted in S230. Then, as the corrective measuring portion 730 sequentially performs the aforementioned procedures for all LEDs-PDs, a driving information table is formed and stored in the correction memory 920. Hence, the concentration measuring portion 720 controls the light intensity according to driving current values for each LED in the driving information table stored in the correction memory 920. In another method, the corrective measuring portion 730 may adjust the LED driving current value until finding the exact LED driving current value that allows a PD output current value to be the same as the reference current value.

Figure 12:
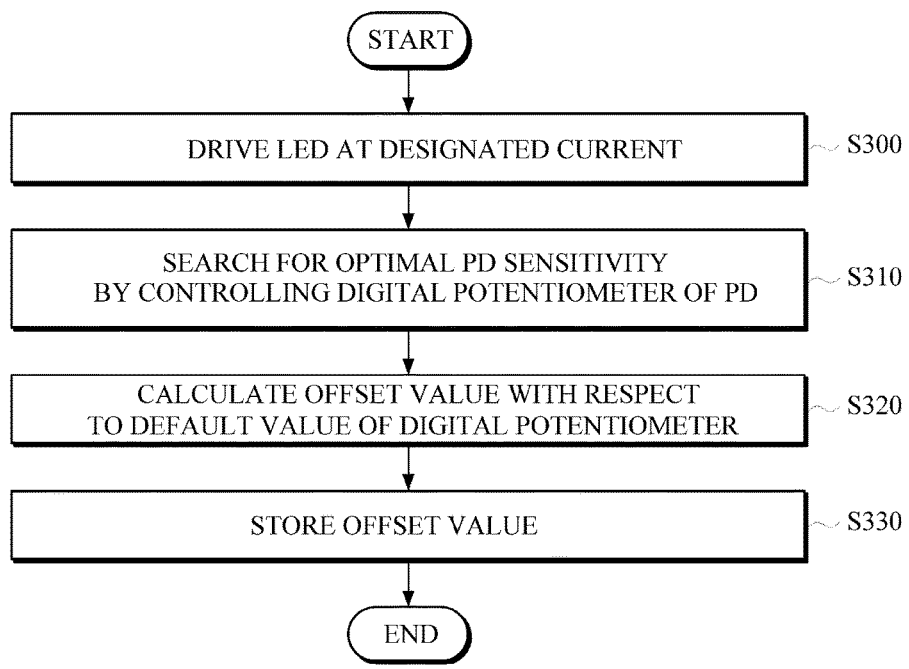
FIG. 12 is a flowchart illustrating a measurement method for identifying sensor characteristics according to another exemplary embodiment.

FIG. 12 is a flowchart illustrating a measurement method for identifying sensor characteristics according to another exemplary embodiment. For identifying the characteristics of sensors, the wells of the microplate 300 may be filled with a standard reagent. Alternatively, the standard agent may be contained in the cartridge 100 and injected into the wells of the microplate 300 through the infusion pumps 200. The corrective measuring portion 730 drives the LED at a designated driving current value, as depicted in S300. Then, the corrective measuring portion 730 searches for an optimal PD sensitivity by adjusting a driving voltage of the PD by controlling a digital potentiometer of the PD, as depicted in S310. Then, after checking the optimal PD driving current value, the corrective measuring portion 730 calculates an offset value with respect to a default driving current value, and stores the offset value, as depicted in S320. As the concentration measuring portion 720 sequentially performs the aforementioned procedures for all LEDs-PDs, an offset information table is formed and stored in the correction memory 920, as depicted in S330. The offset information table is used by the concentration measuring portion 720. The concentration measuring portion 720 performs optical measurement with a fixed digital potentiometer value for output signals of the PDs and thereafter calibrates a measurement value by reflecting the offset to the measurement value. In this case, optical measurement may be performed by the auxiliary controller and the calibration of the measurement value may be performed by the primary controller.

The aforementioned measurement methods for identifying sensor characteristics may be performed only once at the beginning of the initialization of the cell metabolism-measuring apparatus. However, sensors wear down as they are used, and hence the user may manually or periodically initialize the apparatus so as to re-identify the sensor characteristics. In addition, after the initialization, the concentration measuring portion 720 may adjust a trigger level of the Schmitt trigger to control the sensitivity of the PDs.

The above apparatus for measuring cell metabolism may basically provide a precise temperature control function. For example, the apparatus may control a heater while measuring a temperature inside the housing 10 by use of a sensor with a resolution of 0.1° C. or greater such that the temperature in the housing 10 can be adjusted to the human body temperature, i.e., 37° C., and may display information about the measured temperature to a display module.

According to the exemplary embodiments as described above, it is possible to realize automation of all procedures, ranging from drug injection into each well of a microplate to measurement of DO concentration and a pH.

In addition, it is possible to allow a user to define various test protocols for each well of the microplate and conduct measurement of DO concentration and a pH.

Furthermore, it is possible to ensure the accurate measurement of fluorescence intensity.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus to measure cell metabolism, comprising:
   an X-Y DRIVING stage table movable horizontally and vertically;
   a microplate comprising wells and mounted on a top of the X-Y DRIVING stage table, wherein each of the wells is configured to accommodate a cell and comprises a dissolved oxygen (DO) sensing film and a hydrogen ion concentration (pH) sensing film;
   a sensor board situated on the top of the X-Y DRIVING stage table and comprising
      pairs of a light emitter for DO detection and a light detector for DO detection, wherein each of the pairs of the light emitter for DO detection vertically corresponds to the DO sensing film in each of the wells which are mounted on the X-Y DRIVING stage table, and
      pairs of a light emitter for pH detection and a light detector for pH detection, wherein each of the pair of the light emitter for pH detection vertically corresponding to the pH sensing film in each of the wells;
   cartridges containing drugs;
   infusion pumps disposed at fixed positions and configured to inject the drugs, which are supplied from the cartridges, through nozzles to the wells of the microplate;
   a signal processor comprising
      a pulse generator configured to generate a pulse of a controlled duration,
      a light emission selector configured to select any one of the light emitters and to output the generated pulse to the selected light emitter,
      a light detection selector configured to select any one of the light detectors,
      an amplifier configured to amplify a signal output from the selected light detector, and
      a waveform shaper configured to shape a waveform of a pulse of the amplified signal and to process an output signal to be sent to the light emitter and an input signal sent from the light detector;
   a memory configured to store user-defined protocols for each of the wells; and
   a controller comprising a protocol setter configured to
      set a user-defined protocol for each of the wells, wherein the user-defined protocol comprises information for automatically performing a measurement process for each of the wells and setting the user-defined protocol to be the same for a group comprising at least two selected wells among the wells,
      control movement of the X-Y DRIVING stage table and control drug injection into each of the wells, and
      measure DO concentration and a pH based on the generated pulse and a time delay of the pulse which is shaped by the waveform shaper in each of the wells at a designated measurement time.

2. The apparatus of claim 1, wherein the DO sensing film and the pH sensing film comprise fluorescent films.

3. The apparatus of claim 1, wherein cartridges are provided on an upper portion of a housing of the apparatus.

4. The apparatus of claim 1, further comprising a sealing cover configured to hermetically seal all of the wells.

5. The apparatus of claim 4, wherein the sealing cover is vertically movable by controlling a drive of the sealing cover.

6. The apparatus of claim 1, further comprising a light shielding plate positioned between the microplate and the sensor board, wherein the light shielding plate comprises holes that correspond to the light emitters and the light detectors for DO detection and for pH detection, respectively.

7. The apparatus of claim 6, wherein the light shielding plate further comprises filters configured to allow light emitted from the DO sensing film and light emitted from the pH sensing film to pass through the holes.

* * * * *